United States Patent
Decitre et al.

(10) Patent No.: US 8,274,282 B2
(45) Date of Patent: Sep. 25, 2012

(54) METHOD FOR ASSEMBLING A HIGH-DYNAMIC AND HIGH-SPATIAL RESOLUTION EDDY CURRENT TESTING HEAD

(75) Inventors: Jean-Marc Decitre, Marcoussis (FR); Thierry Sollier, Antony (FR)

(73) Assignee: Commissariat a l'Energie Atomique, Paris (FR)

( * ) Notice: Subject to any disclaimer, the term of this patent is extended or adjusted under 35 U.S.C. 154(b) by 1174 days.

(21) Appl. No.: 11/815,293

(22) PCT Filed: Jan. 27, 2006

(86) PCT No.: PCT/FR2006/050069
§ 371 (c)(1), (2), (4) Date: May 9, 2008

(87) PCT Pub. No.: WO2006/082334
PCT Pub. Date: Aug. 10, 2006

(65) Prior Publication Data
US 2010/0139081 A1    Jun. 10, 2010

(30) Foreign Application Priority Data

Feb. 4, 2005 (FR) .................................. 05 50346
Apr. 8, 2005 (FR) .................................. 05 50917

(51) Int. Cl.
*G01R 33/00* (2006.01)

(52) U.S. Cl. ......... 324/262; 324/222; 324/223; 324/228; 324/229; 324/232; 324/234; 324/236; 324/238; 324/239; 324/240; 324/243

(58) Field of Classification Search ................... 324/222, 324/223, 228, 229, 232, 234, 236, 238, 239, 324/240, 243
See application file for complete search history.

(56) References Cited

U.S. PATENT DOCUMENTS

| | | | |
|---|---|---|---|
| 3,430,134 A * | 2/1969 | Flaherty et al. | 324/243 |
| 3,582,772 A * | 6/1971 | Hammer | 324/222 |
| 3,875,502 A | 4/1975 | Neumaier et al. | |
| 3,995,211 A | 11/1976 | Yamada et al. | |
| 4,048,847 A * | 9/1977 | Alers et al. | 73/596 |
| 4,053,828 A * | 10/1977 | Ambler et al. | 324/239 |
| 4,286,216 A * | 8/1981 | Auld et al. | 324/237 |
| 5,182,513 A * | 1/1993 | Young et al. | 324/232 |
| 5,214,727 A * | 5/1993 | Carr et al. | 385/22 |
| 5,537,036 A * | 7/1996 | Sato et al. | 324/239 |
| 6,310,476 B1 * | 10/2001 | Kawanami et al. | 324/241 |
| 6,819,210 B2 * | 11/2004 | Boynton et al. | 335/299 |
| 7,414,404 B2 * | 8/2008 | Keene | 324/329 |

(Continued)

FOREIGN PATENT DOCUMENTS
DE    31 39 491    4/1983
(Continued)

*Primary Examiner* — Patrick Assouad
*Assistant Examiner* — Lamarr Brown
(74) *Attorney, Agent, or Firm* — RatnerPrestia

(57) ABSTRACT

The invention concerns a method for producing an assembly of at least one transmission coil ($B_1$) and one reception coil ($B_2$) for eddy current testing, the reception coil receiving in the absence of fault a complex amplitude signal $V_R$, subject to a variation $\delta V_R$ in the presence of a characteristic fault to be detected. The method consists in selecting the distance $\Delta_{ER}$ between the axes of the transmission coil and the reception coil so as to maximize the ratio $|\delta V_R/V_R|$.

18 Claims, 9 Drawing Sheets

U.S. PATENT DOCUMENTS

| | | | |
|---|---|---|---|
| 8,063,631 B2* | 11/2011 | Fermon et al. | 324/235 |
| 8,159,217 B2* | 4/2012 | Decitre | 324/241 |
| 2002/0047706 A1* | 4/2002 | Looijer | 324/240 |
| 2002/0093330 A1* | 7/2002 | Crouzen et al. | 324/240 |
| 2003/0080736 A1* | 5/2003 | Batzinger et al. | 324/238 |
| 2006/0226833 A1* | 10/2006 | Kubotera et al. | 324/236 |
| 2006/0290349 A1* | 12/2006 | Na et al. | 324/228 |
| 2007/0126422 A1* | 6/2007 | Crouch et al. | 324/240 |
| 2009/0206831 A1* | 8/2009 | Fermon et al. | 324/240 |
| 2010/0109658 A1* | 5/2010 | Decitre | 324/240 |
| 2010/0134100 A1* | 6/2010 | Decitre | 324/241 |
| 2010/0181998 A1* | 7/2010 | Schulz | 324/239 |

FOREIGN PATENT DOCUMENTS

| | | |
|---|---|---|
| EP | 1 022 563 | 7/2000 |
| FR | 2 412 841 | 7/1979 |

* cited by examiner

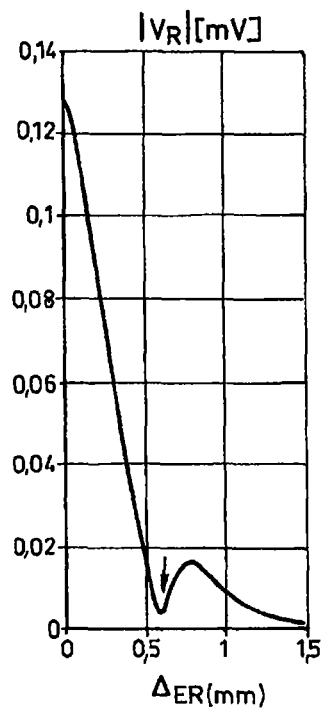
FIG_1a
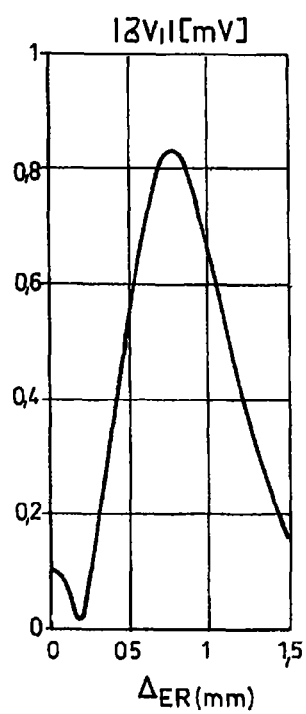
FIG_1b
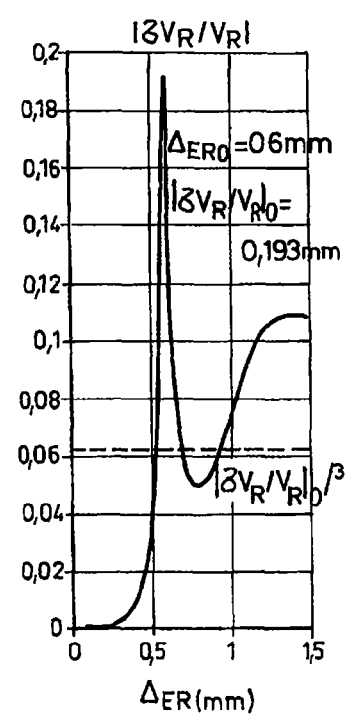
FIG_1c

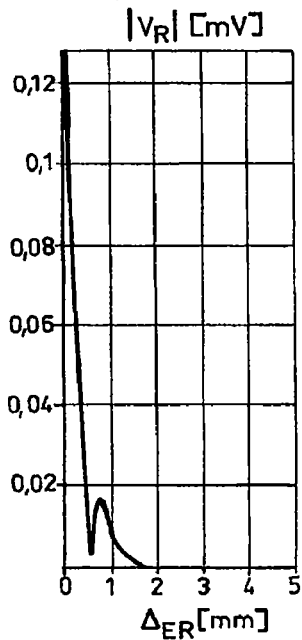
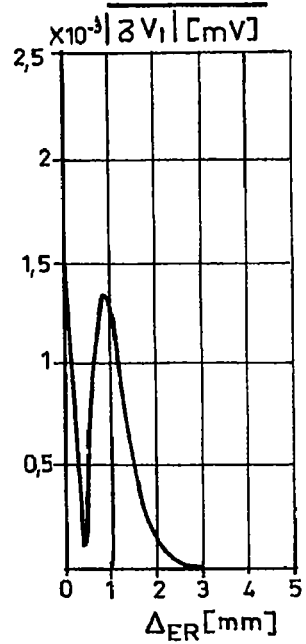
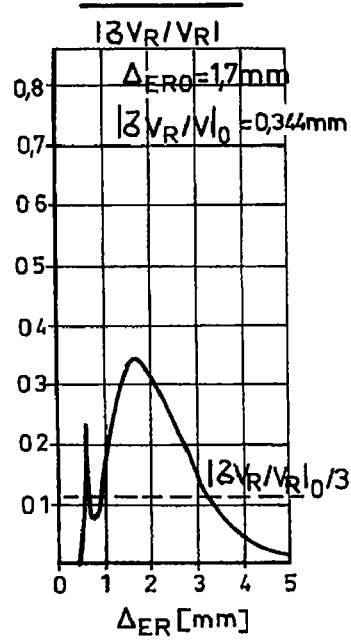
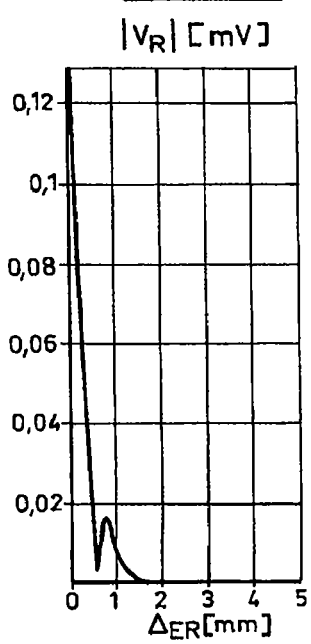
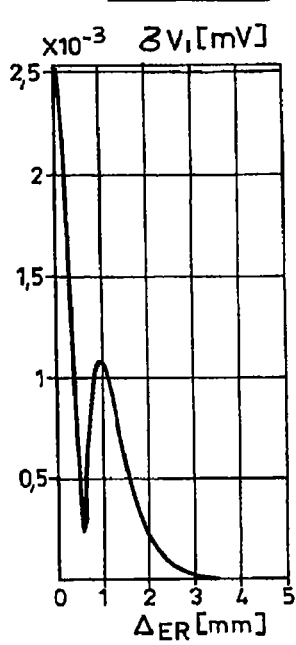
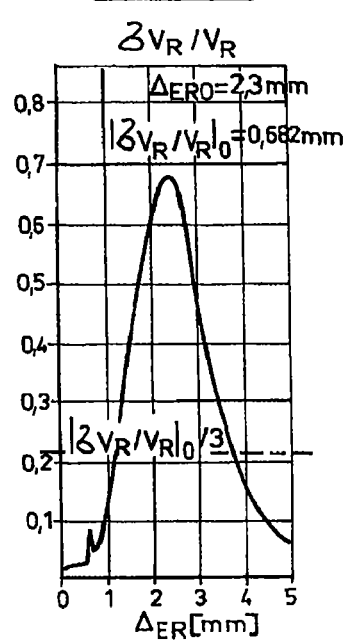

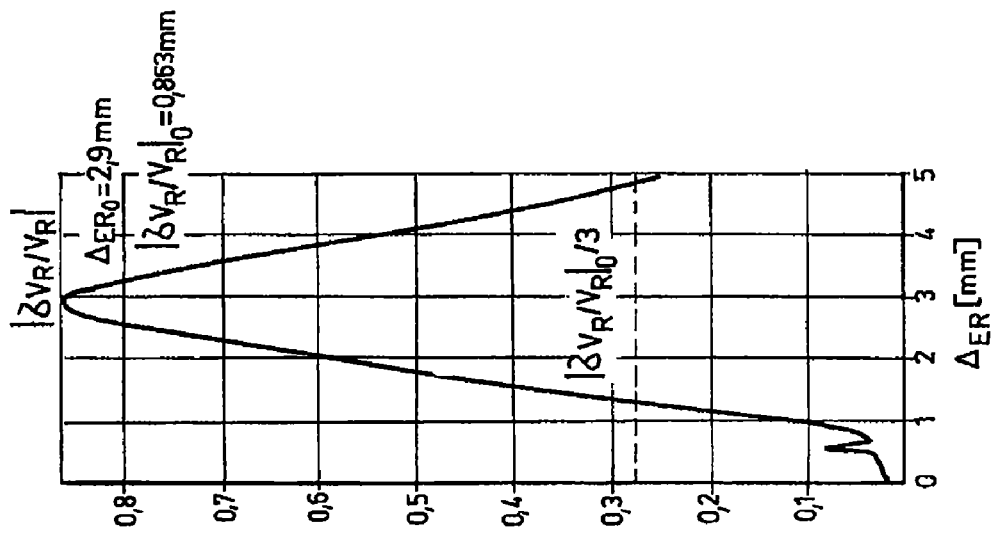
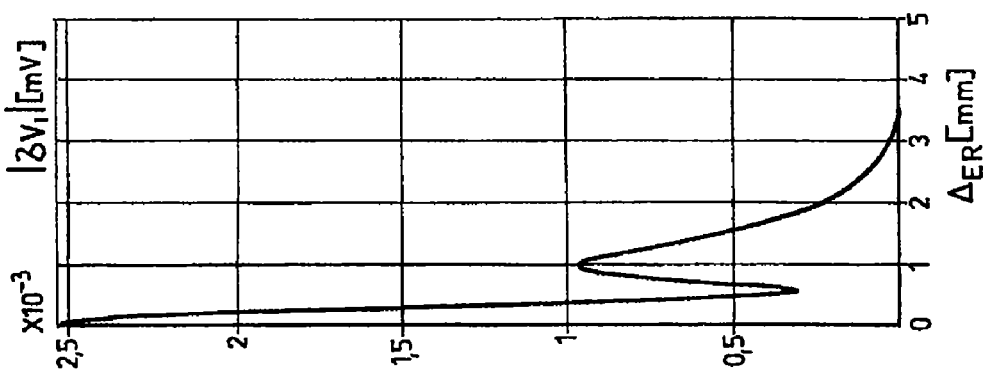
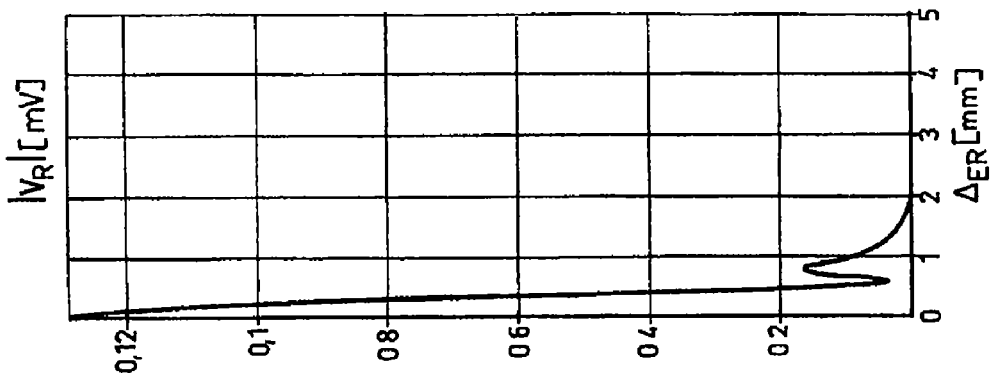

FIG_5a
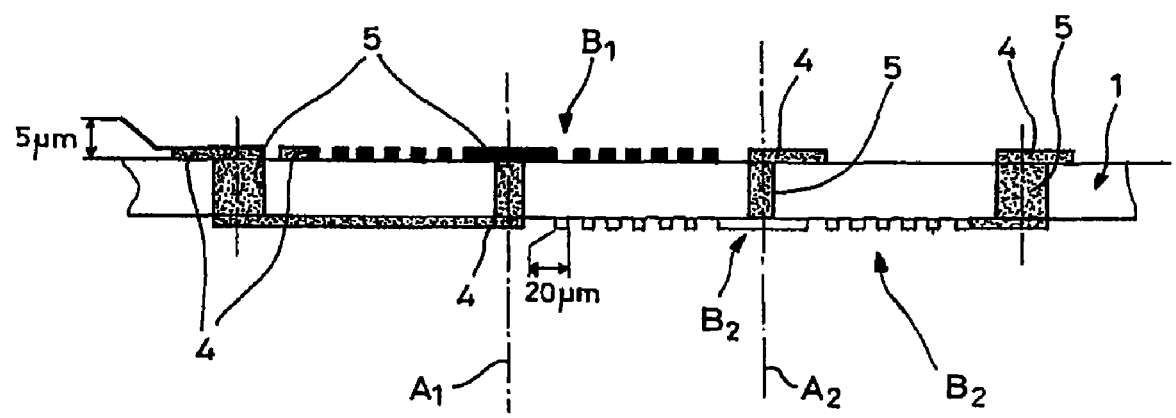
FIG_5b
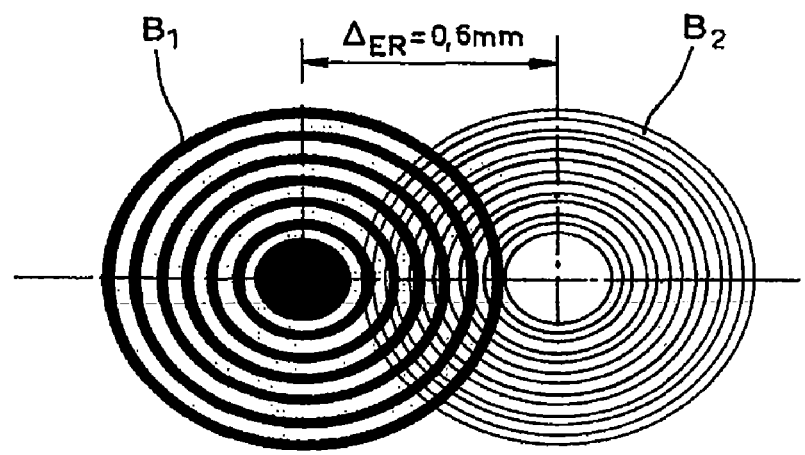

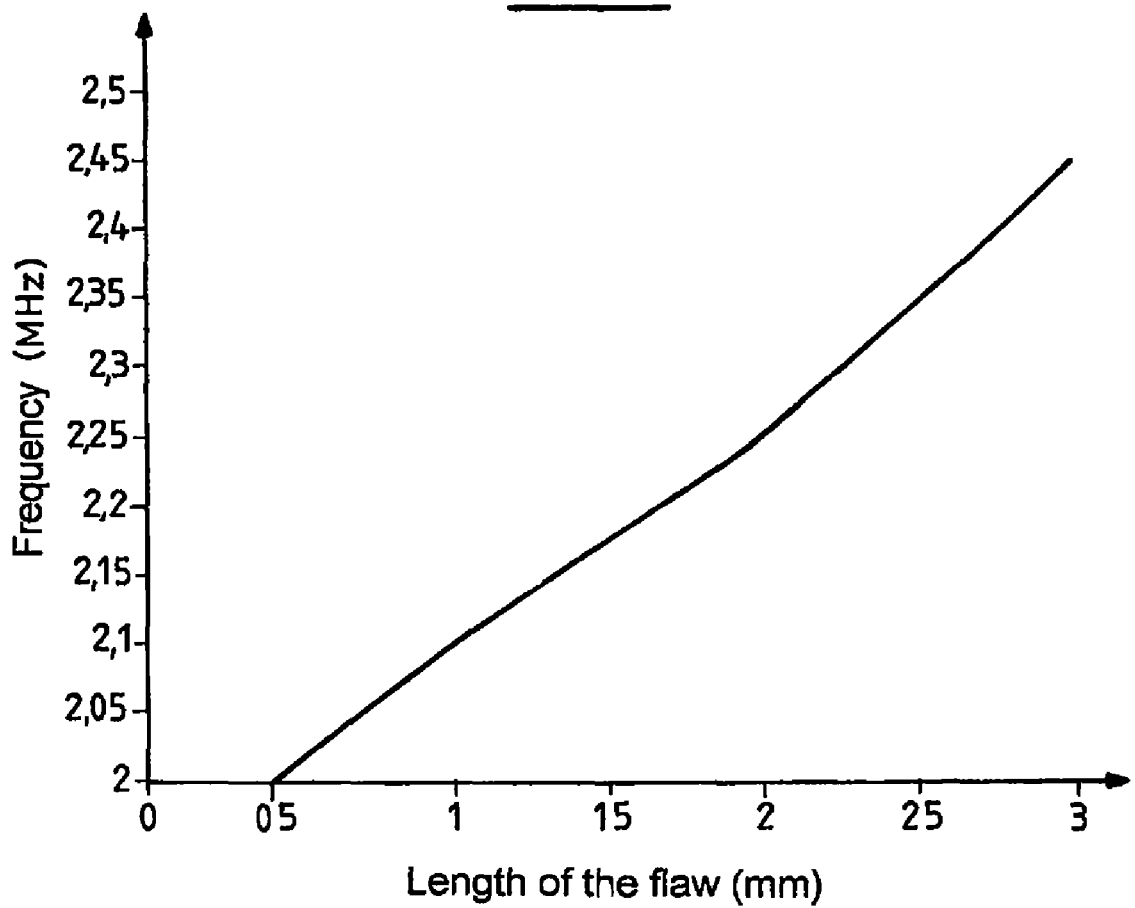
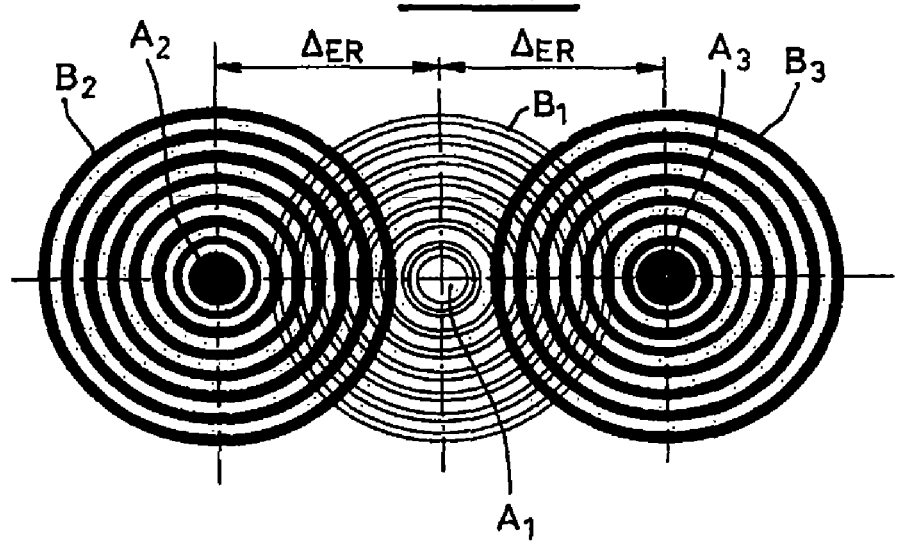

FIG_7b
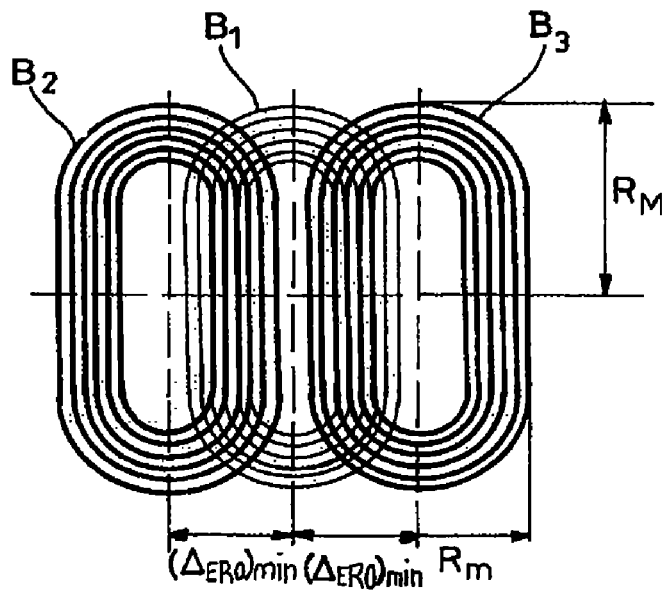
FIG_7c
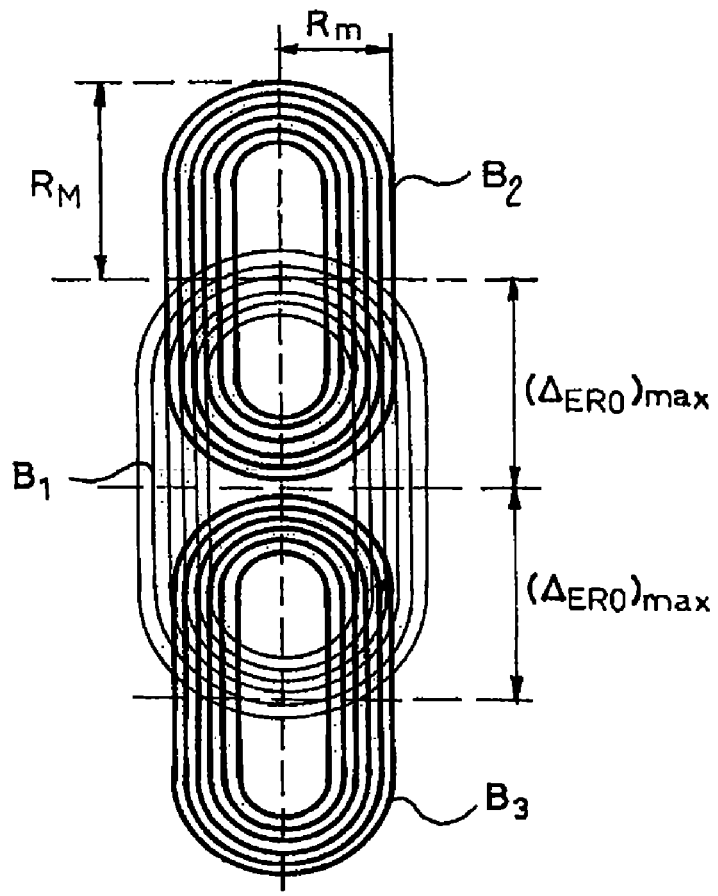

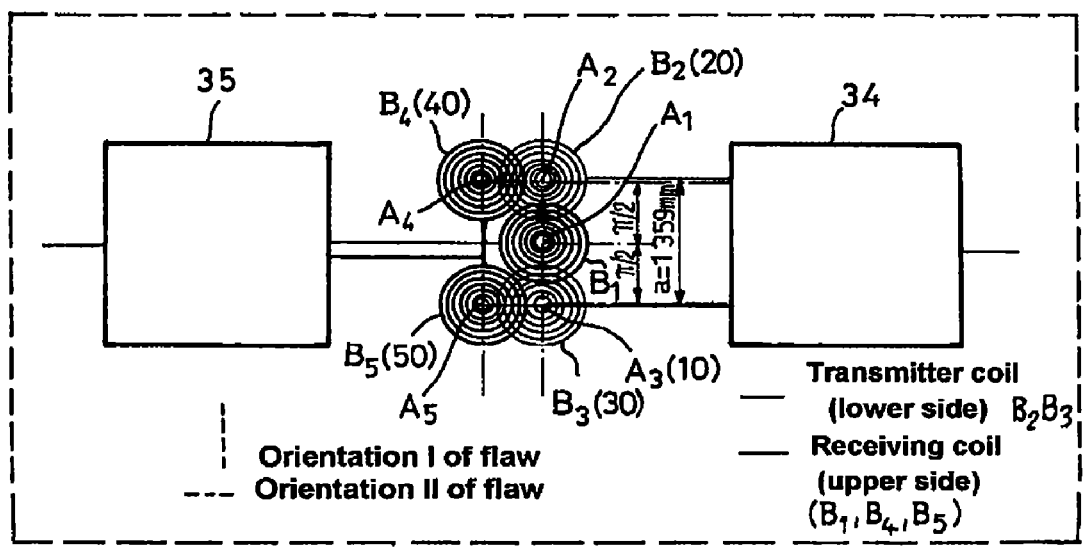
FIG_8a
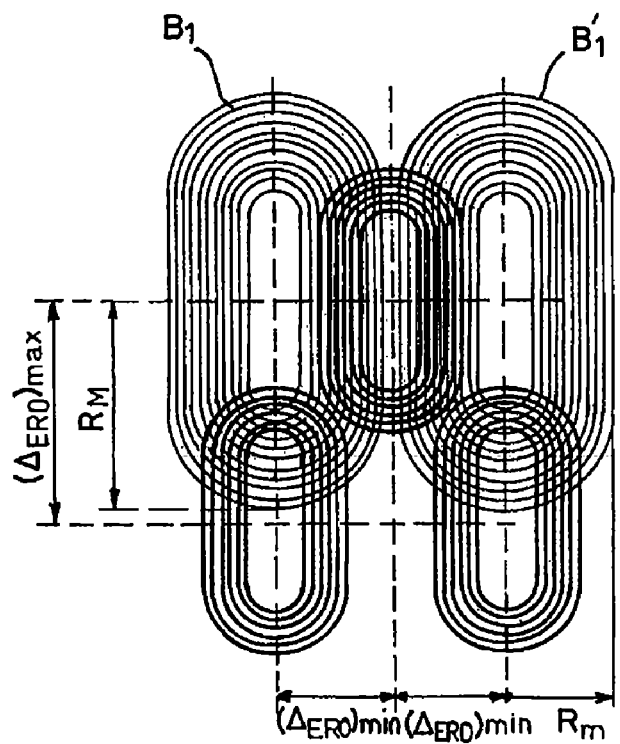
FIG_8b

FIG_9
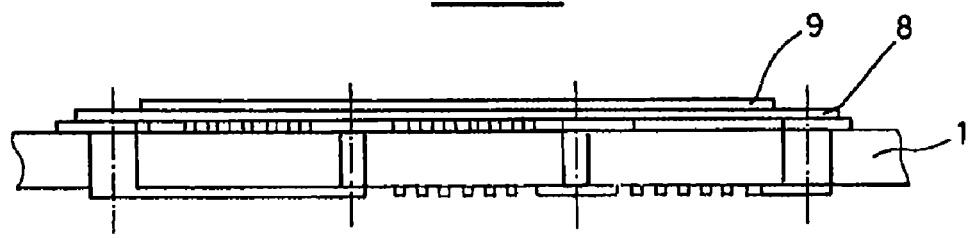
FIG_11
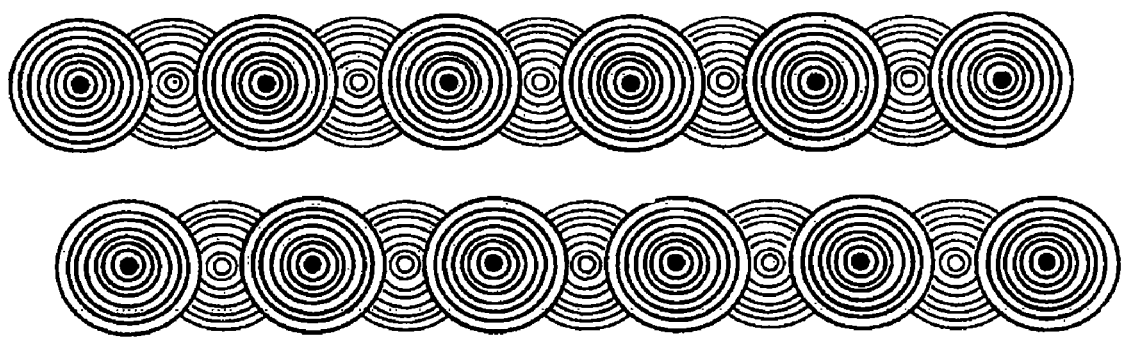

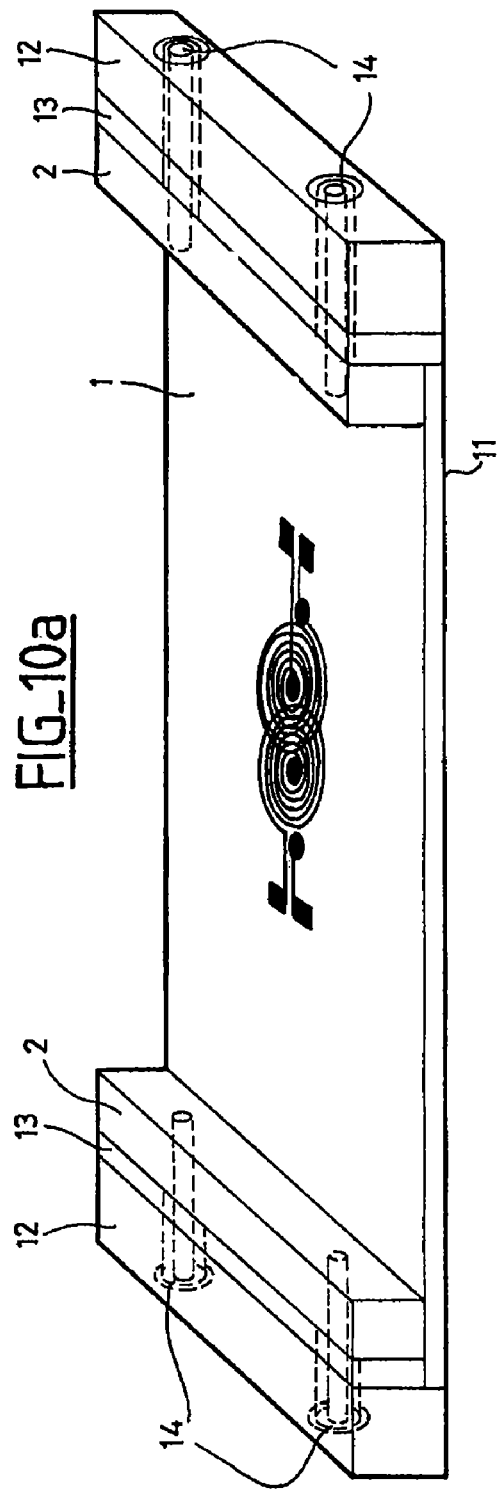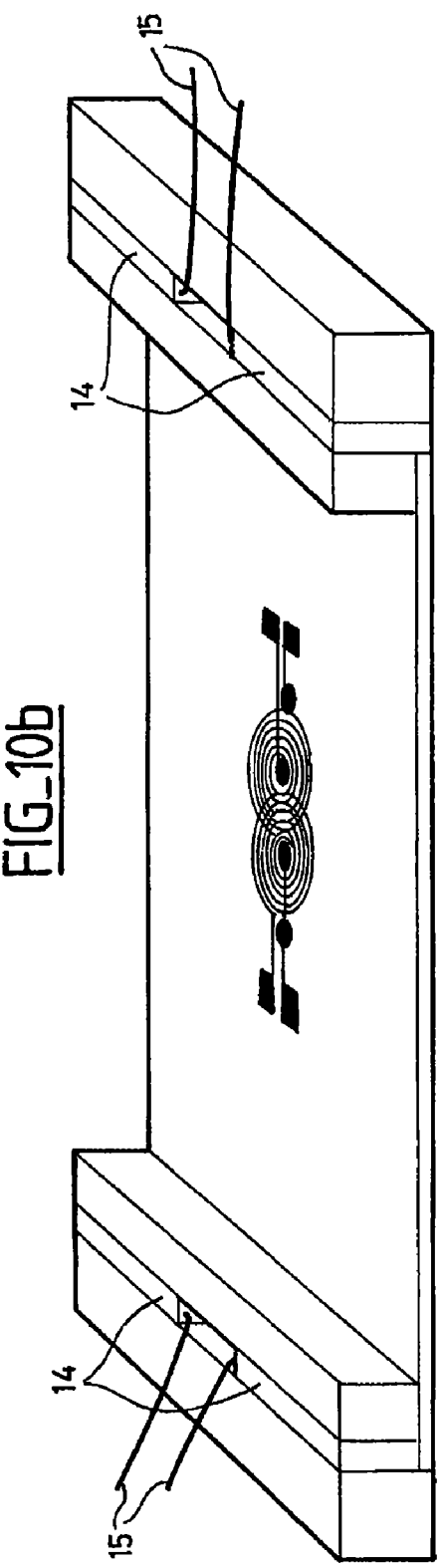

METHOD FOR ASSEMBLING A HIGH-DYNAMIC AND HIGH-SPATIAL RESOLUTION EDDY CURRENT TESTING HEAD

This invention relates to an eddy current testing method with separate transmission/reception functions and high operating dynamics. It also enables to carry out tests using a very compact transmission and receiving coil assembly. Hence, it is particularly advantageous for the detection of miniature flaws, namely for the non-destructive testing (NDT) of mechanical conductor parts.

Definition: in accordance with widespread use, when the transmission or receiving coils are embodied on a printed circuit board, their geometrical shape is referred hereunder as "pattern"; this term is also used to describe the combinations of several coils designed to operate together (e.g. a transmitter and two receivers located on either side).

Furthermore, the term "emf" (abbreviation of electromotive force) shall be used to describe voltage induced inside a coil via a variation in the electromagnetic field passing through it.

It is known that a flaw may significantly alter the mechanical resistance of a part of reduced thickness, even if small in size.

It is recalled that the principle of detecting flaws via eddy currents inside a conducting element consists of emitting, within the vicinity of such element, by using an transmitter coil, an electromagnetic field having a frequency adapted to the conductivity of such material and to the depth of the flaws being located. On the one hand, an electromotive force is measured on the terminals of the receiving coil coming from the direct coupling of the magnetic field lines between the transmitter coil and the receiver coil in company of the conductor element and, on the other hand, a minor variation of the electromotive force which is superimposed upon existence of a flaw in the material. The invention is limited to methods that use at least one coil allocated to the transmission of the electromagnetic signal, capable of generating eddy currents inside the material to be tested, and at least one coil destined for the reception of signals induced by the eddy currents (configuration referred to as "having separate functions").

The $V_R$ electromagnetic force induced in the terminals of each receiving coil is, of course, at the same frequency as the $I_E$ current transmitted inside the associated transmission coil, and requires demodulation in order to obtain the right signal. Furthermore, this $V_R$-induced electromotive force shows signs of strong variation when approaching a part without a flaw at working distance. Faced with a flaw, the induced $V_R$ complex electromotive force becomes $V_R \pm \delta V_R$, with only the $\delta V_R$ variation, very weak in comparison to $V_R$, bearing any information. In practice, the $|\delta V_R/V_R|$ ratio determines the quality of the measure and the sensitivity of the method.

The detection electronics must therefore demonstrate high operating dynamics. Taking account of the technological possibilities, such constraint strongly limits, in the prior art, the possibility to detect minor flaws, especial when these are poorly orientated.

The possible flaws in the material to be tested are not only easy to detect, but also modify further the circulation of eddy currents. Such currents circulate within the thickness of the material to be tested, along a run comparable with the current lines of the inducing coil, though in the opposite direction. It is easier to detect flaws extending along the plane formed by the axes of the transmitter coil and receiving coil and located in between them (flaws referred to as "type I"). Conversely, it is difficult to detect flaws extending along the transmitter plane located within the plane formed by the axes of the two coils (flaws referred to as "type II").

In order to limit such incidence of the random orientation of flaws upon their detection, many methods and devices have been embodied, either by performing several measures in succession through scanning with the measuring device according to the orthogonal directions, or by multiplexing several transducers. It generally involves transmitter and receiver matrixes assembled on a same measuring head, so that a same flaw is orientated first of all towards the field lines going from a first transmitter to a first receiver, then in a second direction, different from the first, the field lines going from the same transmitter to a second receiver or even from a second transmitter to a second receiver.

In the latter case, nevertheless, improvement of detection is generally obtained through the accumulation of a large number of coils on a small surface, even though such layout creates crosstalk problems. We could then resort to a relative wide spacing of the patterns between each other (which would limit the density of the patterns), or even to a multiplexing of the patterns' transmitters and receivers (which would lead to maximal density of the patterns but to a slowing-down of the measure). The resolution remains in any case limited due to the distance between the coils of a same pattern, itself limited due to their outer radius.

To resume, the real principle of eddy current testing leads to the detection of minute $\delta V_R$ complex variations of $V_R$, around the much larger $V_R$ value, the latter varying in large proportions with the distance of the coils in relation to the element to be tested and to their relative orientation; it also varies, though on a lower scale, with the conductivity of such element, a high conductivity being more beneficial. Such difficulty, made worse by the small size of the flaws to be detected, is also hindered by their orientation.

Another characteristic of detecting minute flaws is the small size of the transducer coils (small patterns), which leads to very low amplitude signals being detected.

In order to remedy such problems, the mechanisms, according to the prior art, work through association of a larger number of coils.

Thus, the U.S. Pat. No. 6,310,476 "Eddy current flaw detector", registered by Mitsubishi, reveals a mechanism with an even number of receiving coils, placed in a symmetric manner in relation to the transmitter coil and connected in a differential manner. Despite the weight and the cost of such mechanism, it also has differential assembly flaws: the undesirable signals are only eliminated if they appear at the same time on the two coils connected opposite each other, with the same amplitude and the same phase. Furthermore, it is also necessary for these two coils and their respective measuring channels to have identical characteristics.

In order to adapt to the curved geometry parts and to scan a large surface area without missing flaws of a certain size, General Electric reveals in its patent EP 0 512 796 A2 "Eddy current probe arrays", a device using matrixes or eddy current sensor modules, the coils of which are mounted on a flexible support in order to remain as near as possible to the flaws when the element to be tested is of curved geometry and are further spatially correlated. The inducers are constituted of two rectangular coils, very much elongated in the orthogonal direction during scanning. Opposite these two inducers are placed two staggered rows of receiving coils facing the coils of the first row. Any flaw located in between the two receiving coils of the first row can be found perpendicular to the coils of the second row depending on the preferred scanning direction, and vice-versa. Nevertheless, despite the cost and the weight of such a device, the flaws that are not easily detected, due to their direction in relation to the first row of coils, maintain this same orientation, and hence this same detection difficulty, in relation to the second row of receiving coils. Finally, this document indicates several methods of embodiment for the coils, as well as how to add reinforcing. The receiving coils receive everything along their whole surface area, the magnetic field lines immediately coming out the corresponding transmitter coil (vast mutual induction).

A second General Electric patent, U.S. Pat. No. 5,262,722 "Apparatus for near surface non-destructive eddy current scanning of a conductive part using a multi-layer eddy current probe array", reveals a device, analogous to the previous one, though with implementation in a multiplexed manner.

In conclusion, the current status of the method and eddy current testing mechanisms do not enable to be certain about the detection of flaws of a size that could harm mechanical parts, especially when the size of the flaws or their orientation hinders their detection.

DISCLOSURE OF THE INVENTION

The invention concerns an embodiment method for an assembly of at least one transmission coil and one receiving coil for eddy current testing, the receiving coil receiving, in the absence of a flaw, a complex $V_R$ amplitude signal, subjected to a $\delta V_R$ variation in the presence of a standard flaw to be detected, characterised in that the $\Delta_{ER}$ distance between the axes of the transmission and receiving coils shall be chosen in order to maximise the $|\delta V_R/V_R|$ ratio.

Each coil is composed of wire windings, generally of varying dimensions. The widest wire winding describes a loop that shall be referred to as "R", i.e. the largest distance in relation to its baric centre. For coils whose axial section has an elongated shape, it is advantageous to introduce two R values: $R=R_M$ according to maximal axis dimension, and $R_m$ according to the minimal axis dimension.

The method according to the invention aims at carrying out eddy current tests by placing and maintaining in between the respective axes $A_1$ and $A_2$ of two flat coils, $B_1$ transmitter and $B_2$ receiver, a distance comparable or equal to $\Delta_{ER}$ thus optimising the $|\delta V_R/V_R|$ ratio characterising the quality of the measure. Such optimisation is thus embodied intrinsically for each transmitter/receiver coil combination positioned in accordance with the method described above.

The method according to the invention intervenes in the design and embodiment of the transducer head, once the characteristics of the material to be tested, the value of the air-gaps e et e' between this part and each one of the coils have enabled determination of the working frequency, as well as the shape and size of the coils whose largest radius is R. According to a preferred embodiment in which the largest distance between the baric centre of the largest size coil and the most elongated point of this coil's largest wire winding is referred to as "R", it comprises the following steps:

a—to determine a frequency value of the excitation current running along the transmission coil, such frequency being determined in a classical manner;

b—to determine a standard flaw to be detected, characterised by its average size and depth in relation to the element to be tested;

c—to use the values obtained in steps a and b, to determine the three following sizes, either through modelling or by experiment:

i) the $V_R$ emf complex induced inside the receiving coil when the $\Delta_{ER}$ distance between the axes of the transmission and receiving coils varies at least within the $\{0; 3R\}$ gap, ii) the $\delta V_R$ variation of the $V_R$ emf complex induced inside a receiving coil for the same $\Delta_{ER}$ distance variation within the gap of at least $\{0; 3R\}$, iii) the $|\delta V_R/V_R|$ variation of the ratio module for the sizes defined in ii) and i), for the same $\Delta_{ER}$ distance variation within the gap of at least $\{0; 3R\}$, d—to trace the $|\delta V_R/V_R|$ ratio curve depending on the $\Delta_{ER}$ distance variation within the gap of at least $\{0; 3R\}$, then determine the maximal $|\delta V_R/V_R|_0$ ordinate and the $\Delta_{ERO}$ abscissa of this maximum, such value constituting the optimal operating point;

e—as an optional and sub-optimal solution, determination of a range of $\{\Delta min; \Delta Max\}$ distances on either side of $\Delta_{ERO}$, for which the $|\delta V_R/V_R|$ ratio corresponds to the third of its maximal value; such range corresponding to what shall be designated subsequently by "a distance comparable or equal to $\Delta_{ERO}$";

f—if the $\Delta_{ER}$ values found either during step d when searching for the optimal criteria, or during step e when searching for the sub-optimal criteria, are not considered acceptable, then the parameters obtained in steps a and b are to be modified;

g—embody the coils or the assembly of coils, in such a manner that the operating point of each receiving coil checks either the optimal criteria of step d or the sub-optimal criteria of step e.

According to a first preferred embodiment, the distance between the respective axes of each transmission/receiving coil combination is fixed and the frequency of the excitation current is adjusted in accordance with the minimal dimension of the average depth of the standard flaws to be detected. In such a case, the excitation electronics must be capable of modifying the working frequency of the electronic means associated with the coils, e.g. every time the size of the standard flaws to be detected is modified, or even if the material of the element to be controlled is changed.

By electronics associated to the coils is meant the electronic means for supplying current to the transmission coil or coils, in order to demodulate and process the signals of the receiving coil or coils, and possibly to add, subtract or multiplex the signals of several coils.

According to a second preferred embodiment, the excitation frequency is constant, and the method according to the invention enables to determine, according to the minimal dimension and the average depth of the standard flaws to be detected, a value, either optimal (step d) or sub-optimal (step e), of the $\Delta_{ER}$ distance between the respective axes of each transmission/receiving coil combination.

According to a first variant of the first or second preferred embodiment, the $\Delta_{ER}$ distance between the respective axes $A_1$ and $A_2$ of two coils, respectively $B_1$ transmitter and $B_2$ receiver, varies within a $\{0; 3R\}$ gap. Such first variant is especially advantageous for detecting small size flaws.

According to a second variant of the first or second preferred embodiment, the $\Delta_{ER}$ distance between the respective axes $A_1$ and $A_2$ of two coils, respectively $B_1$ transmitter and $B_2$ receiver, varies within a gap exceeding $\{0; 3R\}$ and preferably equal to $\{0; 9R\}$. In such a case, there generally exists, for abscissa above 3R, a second maximum of the $|\delta V_R/V_R|$ ratio when $\Delta_{ER}$ varies. This second maximum is increased, just as the standard flaw to be detected is larger. This second maximum for the $\Delta_{ERO2}$ abscissa and $|\delta V_R/V_R|_2$ ordinate corresponds to a second range of values $\{\Delta min; \Delta Max\}$ on either side of $\Delta_{ERO2}$, for which the $|\delta V_R/V_R|$ ratio is equivalent to the third of its $|\delta V_R/V_R|_2$ maximal value. This variant is advantageous for seeking large-size flaws while blacking out the small-size flaws and reducing the risk of artefacts by as much.

According to a third variant of the second preferred embodiment, the $\Delta_{ER}$ distance between the respective axes $A_1$ and $A_2$ of two coils, respectively $B_1$ transmitter and $B_2$ receiver, is embodied during step g in an adjustable manner. In such a case, the transmitter coils are on a first base, e.g. a first printed circuit board, and the receiving coils are on a second base, e.g. a second printed circuit board, with the two bases being able to be moved one in relation to the other due to a means for sliding. Such means enable, not only an adjustable sliding from the relative position of the two bases, but also its steadfastness during the measuring phases, once the head testing has been performed. These may be passive of the mechanical type (e.g. with a screw and/or a runner), or active comprising at least one micro-actuator (e.g. piezoelectric).

When the coils have an elongated axial section, the widest wire winding having a large radius $R_M$ and a small radius $R_m$, the following variant may be applied to each of the embodiment methods described above. Within the plane comprising the axis of the coil and the big $R_M$ radius, the application of the invention enables to define a first optimal distance $(\Delta_{ERO})_{Max}$ and a range of associated values $\{\Delta min; \Delta Max\}_{Max}$, while within the plane including the coil's axis and the small $R_m$. radius, the invention enables to define a second associated optimal distance $(\Delta_{ERO})_{min}$ and a second range of values $\{\Delta min; \Delta Max\}_{min}$. The existence of several optimal distances according to several axes thus enables to embody patterns where the coils are not necessarily at the top of squares or diamonds. Such a variant shall be subsequently illustrated through FIGS. 7b, 7c and 8b.

Step c of the method may be determined either by modelling or by experiment using an analogous device to the one described above as an example. The two flat coils B1 for transmission and B2 for reception are embodied, each one on a printed circuit board of reduced thickness in kapton, of identical dimensions: 6 wire windings in flat wire winding, of which the widest has a 0.5 mm R radius and the smallest has the diameter of the central metallic hole serving for passing the connection. They may also be slipped one against another. The respective axes $A_1$ and $A_2$ of $B_1$ and $B_2$ can thus represent a variable $\Delta_{ER}$ distance between them. A standard flaw shall be fixed, corresponding either to the smallest flaw that is to be detected or to the flaw considered to be representative. In the example, an elongated parallelepiped flaw in accordance with a main direction, measuring 0.4 mm in accordance with such direction, and 0.1 mm in width (parallel to the surface) and 0.2 mm in depth in accordance with the other directions. It will flush the surface of the part to be tested. The orientation used for modelling or experimentation is the one which maximises the probability of detection; the 0.4 mm length is centred on the axis linking the coil centres. The part to be controlled has a $\sigma$ conductivity of 1 MS/m and a thickness of 3 mm. The working frequency chosen shall be equal to 2 MHz.

The transmission/receiving coil combination is then placed in front of the element to be inspected, at a distance e from the nearest coil (e.g. the receiving coil) and at e' for the other coil, the distance e'-e being the sum of the axial length of the nearest coil and of the thickness of the support. Such distance e has been chosen using the usual practices of eddy current testing. The transmitter coil is excited by an $I_E$ current with an adequate frequency for inducing eddy currents. The receiving coil is thus the seating of a $V_R$ electromotive force induced in its terminals.

The $\phi$ phase represented by $V_R$ in relation to $I_E$ changes between the position where the $A_1$ and $A_2$ axes are practically merged and the position where such axes are distant by approximately twice R or slightly more. Between these two positions, there exists an intermediary position where the $\phi$ varies very abruptly and where the $|V_R|$ module passes through a minimum. When the distance between the $A_1$ and $A_2$ axes is increased again, the electromotive force module increases once more without reaching a value as high as that of the first maximum, then decreases, but with a phase which varies more slowly. FIG. 1a illustrates the $|V_R|$ module of the complex value of the $V_R$ electromotive force induced in the terminals of the receiving coil when the $\Delta_{ER}$ distance is varied between the axes of the transmitter and receiver coils. It is traced for a $\Delta_{ER}$ variant within the $\{0; 3R\}$ gap, the value of the air-gap is e=0.1 mm and e'=0.15 mm, and the conductivity of the element is $\sigma$=1 MS/m. For a $\Delta_{ER}$ nil distance, the coils have the same axis and the $V_R$ complex amplitude of the electromotive force gathered on the receiving coil terminals is of course maximal. When $\Delta_{ER}$ increases, such amplitude falls very quickly in order to pass through a first minimum, as indicated in the figure by an arrow, and the phase very quickly varies by approximately 180°. Failing any conductor element in front of the transducer coils, the $V_R$ electromotive force is cancelled in order to change direction, and the $\phi$ phase tips almost instantly by 180°.

In front of a $\sigma$ conductivity element located at e distance from the transducer coils (which are within the planes extremely near to each other), the phase variation is less abrupt, in accordance with a profile dependant upon the $\sigma$ and e values, and the $V_R$ complex amplitude module passes through a minimum which is no longer equal to zero, and whose position and value depend especially on the $\sigma$ values, the e air-gaps and the frequency. In the presence of an element to be controlled, it is the apparition of an imaginary component, not being cancelled for the same abscissa as the real component, which has the effect of shifting the position of this minimum and of making its value other than nil.

Such minimum of the $V_R$ complex amplitude module makes detection much easier for a minor $\delta V_R$ variation around $V_R$. Nevertheless, it is not directly the $V_R$ minimum which determines the quality of the measure and the dynamics, but rather the $|\delta V_R/V_R|$ ratio. It is this ratio which must be the greatest possible, and which it is necessary to maximise when $\sigma$ and e vary.

Thus an elongated standard flaw is chosen according to a main direction measuring, for example, 0.4 mm, its other dimensions being negligible. After FIG. 1a, and for the same air-gap parameters, and the same $\Delta_{ER}$ variation field within the $\{0; 3R\}$ gap, the 1b curve of the $\delta V_R$ electromotive force variations, induced by the standard 0.4 mm flaw, can be read as an experiment when $\Delta_{ER}$ varies ($\Delta_{ER}$ being in abscissa and $\delta V_R$ in ordinates). The quality of the measure is then represented by a third curve 1c illustrating the $|\delta V_R/V_R|$ ratio variations (in ordinates) according to the $\Delta_{ER}$ variations (in abscissa). On this curve can be read the $|\delta V_R/V_R|_0$ ordinate of the first maximum, which corresponds to the optimal operating point representing the greatest possible measuring dynamics. The corresponding abscissa is thus the optimal $\Delta_{ERO}$ value of the $\Delta_{ER}$ distance.

It is necessary to note that this optimal operating point does not quite correspond to the $|V_R|$ minimal value, which itself does not quite correspond to the value which cancels the mutual induction when there are no elements to be controlled facing the transducer coils.

On either side of the optimal $|\delta V_R/V_R|_0$ ordinate operating point can be read the points whose ordinates correspond to the third of $|\delta V_R/V_R|_0$, the first $\Delta min$ abscissa corresponding to the minimal distance for which operating is close to optimum, and the second $\Delta Max$ abscissa corresponding to the maximal distance for which operating is close to optimum. The $\{\Delta min,$ ΔMax} gap constitutes the distance range for which operating is either optimal or sub-optimal, close to optimum.

The method according to the invention for the embodiment of a transducer coil assembly, comprising at least one $B_1$ transmitter coil and a $B_2$ receiver coil, enabling numerous variants and combinations as soon as, for each transmission/receiving coil combination, their $A_1$ and $A_2$ axes are separated by a $\Delta_{ER}$ distance comprised within the {Δmin, ΔMax} distance range. Preferably, the coils are flat, i.e. their axial length being lower than the largest radius of their largest wire winding.

With this same device, the second variant of the second preferred embodiment is easily revealed, whereupon the $\Delta_{ER}$ variation range is wider than 3R. As shown in FIGS. 2a, 2b and 2c, there exists a second $|\delta V_R/V_R|$ maximum for abscissa exceeding 3R. Its amplitude increases with the size of the flaws that are trying to be detected, as shown in the successive FIGS. 2, 3 and 4.

FIGS. 2a, 2b and 2c are analogous to FIGS. 1a, 1b and 1c, although they are traced for $\Delta_{ER}$ varying within the {0; 10R} gap, the value of the air-gap (e=0.1 mm and e'=0.15 mm) and the conductivity of the element (σ=1 MS/m) remain the same, although the main length of the flaw is, in this case, at 1 mm compared with 0.4 mm in FIG. 1. FIGS. 3a, 3b and 3c are analogous to FIGS. 1a to c, although the main length of the flaw is, in this case, at 2 mm. FIGS. 4a, 4b and 4c are analogous to the preceding figures with a main length of the flaw at 3 mm. These three figures show, on the one hand, the existence of a second maximum whose amplitude increases with the size of the standard flaw to be detected and, on the other hand, that it is not useful to increase $\Delta_{ER}$ above 9R.

Besides these precisions, it is recalled that for the other characteristics, such as the excitation frequency of the transmitter coils, the coil's dimensions and their type (e.g. made of wiring, with or without a core, or made of printed technology), the choices are made taking account of the material to be tested, of the size and depth of the flaws sought after, and taking heed of the prior art for eddy current testing methods.

Although the method intrinsically gives each transmission/receiving coil combination the possibility to practically cancel the $V_R$ electromotive force induced on the receiving coil terminals, it is possible to choose, depending on a first variant, either to use an transmission coil and two receiving coils located symmetrically and connected opposite each other, or two transmission coils located symmetrically in relation to a same receiving coil and connected opposite each other. Thus is embodied a differential device, though exempt of the main flaw of the differential devices which do not implement the method.

Indeed, these flaws result from the necessity to have perfect symmetry, not only with regard to the signals to be eliminated, but also for the two channels connected in a differential manner. According to the invention, the $V_R$ electromotive force induced on the terminals of each receiving coil is intrinsically very close to zero with the gradient of the curve representing $|V_R|$ in accordance with $\Delta_{ER}$ being cancelled in $\Delta_{ERO}$, thus making it very weak in the vicinity of this optimal point, which considerably reduces the effects of a possible dissymmetry of the signals to be eliminated or of the characteristics of the coils and measuring channels connected as differential.

According to a simplified variant of the invention method which can be cumulated with all other variants, it is considered that for the $\Delta_{ER}$ distances near to $\Delta_{ERO}$, the $|V_R|$ variations depending on $\Delta_{ER}$ are sufficiently weak to be neglected. In such a case, the maximum of the $|\delta V_R/V_R|$ ratio, when $\Delta_{ER}$ varies, can be approximated through the $|V_R|$ maximum when $\Delta_{ER}$ varies. In such a case steps c, d and e of the method can be written in an equivalent manner:

c'—to use the values obtained during steps a and b, determine, either by modelling or by experiment, the $\delta V_R$ variation of the $V_R$ emf complex induced inside a receiving coil when the $\Delta_{ER}$ distance between the axes of the transmission and receiving coils varies at least within the {0; 3R} gap;

d'—to trace the curve of $|\delta V_R|$ according to the $\Delta_{ER}$ distance variation within the gap of at least {0; 3R}, then determine the maximal $|\delta V_R|_0$ ordinate and the $\Delta_{ERO}$ abscissa of this maximum, such value constituting the optimal operating point;

e'—as an optional solution, determine a range of {Δmin; ΔMax} distances on either side of $\Delta_{ERO}$, for which the $|\delta V_R|$ ratio corresponds to the third of its maximal value.

A privileged application of this variant consists of determining, as above, the $\Delta_{ERO}$ optimal value of $\Delta_{ER}$ or a sub-optimal value comprised within the {Δmin; ΔMax} gap, then when certain conditions of use vary, such as the type of the element to be controlled or the size of the flaws, this variant shall be used in order to adjust the $\Delta_{ER}$ distance.

More elaborated combinations shall be subsequently explained in the detailed description.

DESCRIPTION OF THE FIGURES

FIGS. 1a, 1b and 1c illustrate, for two flat coils $B_1$ and $B_2$ having the same radius and moving according to the parallel planes in order for their $\Delta_{ER}$ entreaxis to increase, how the $|V_R|$ module of the complex tension, induced on the terminals of the receiving coil (FIG. 1a), varies, the $|\delta V_R|$ signal induced by a flaw measuring 0.4 mm in length (FIG. 1b) and by the $|\delta V_R/V_R|$ ratio between these two dimensions, thus determining the sensitivity of the method, FIGS. 2a, 2b and 2c are analogous to FIGS. 1a, 1b and 1c, but for a flaw measuring 1 mm in length, FIGS. 3a, 3b and 3c are analogous to FIGS. 1a, 1b and 1c, but for a flaw measuring 2 mm in length, FIGS. 4a, 4b and 4c are analogous to FIGS. 1a, 1b and 1c, but for a flaw measuring 3 mm in length, FIGS. 5a and 5B schematically illustrate the two coils in an elementary eddy current measuring system, according to the invention, FIG. 6 shows the variations required for the excitation frequency in order to preserve a same $\Delta_{ERO}$ optimal distance when the main dimension of the flaw varies, FIGS. 7a, 7b and 7c schematically illustrate the three coils in an embodiment variant of an eddy current measuring system, according to the invention, FIGS. 8a and 8b schematically illustrate the five coils in an embodiment variant of an eddy current measuring system, according to the invention, FIG. 9 schematically illustrates a variant of the system represented in FIG. 5a comprising the addition of a ferromagnetic ribbon in order to channel the lines of the magnetic fields between the transmitter and the receiver, FIGS. 10a and 10b schematically illustrate two embodiment methods where the $\Delta_{ER}$ distance between the coils is adjustable mechanically (FIG. 10a) or by a piezoelectric micro-actuator (FIG. 10b), FIG. 11 represents an example of matrix association according to the invention method for several transmission/receiving coil combinations.

DETAILED DESCRIPTION OF THE PREFERRED EMBODIMENTS

According to the preferred embodiment implemented through the invention, the main parameters are those detailed in the explanation of step c.

The element to be tested has a σ conductivity of 1 MS/m and a thickness of 3 mm. The coils are air-borne, directly engraved on the two sides of a same flexible printed circuit board made of 50 μm-thick kapton. A protective Teflon film 100 μm thick is applied onto the kapton face in contact with the target, thus ensuring electrical insulation and mechanical protection. The air-gap e is thus 0.1 mm for the receiving coil, with e' equaling 0.15 mm for the transmitter coil.

In order to ensure the detection of such flaws, a same pattern for the transmission and receiving coils shall be chosen, composed of a coil plane, the largest diameter of which being 1 mm, and comprising 6 coils engraved in 5 μm-thick copper, the smallest coil being the diameter of a metallic hole ensuring the electric connection, i.e. 0.25 mm approximately.

The corresponding working frequency is around 2 MHz.

An elongated standard flaw is trying to be detected, as per a main direction, and measuring 0.4 mm in accordance with such direction (the other dimensions of the flaw being 0.1 mm and 0.2 mm as above). It will flush the surface of the element to be tested. Such element has a σ conductivity of 1 MS/m and a thickness of 3 mm.

An $I_E$ current equal to 20 mA is considered inside the transmitter coil; the $|V_R|$ model of the complex tension induced inside the receiving coil is then equivalent to μV when $\Delta_{ER}$ is within the $\{\Delta min; \Delta Max\}$ gap.

Modelling according to the first variant of the second preferred embodiment gives the curve lines in 1a, 1b and 1c for a $\Delta_{ER}$ distance between the axes of the transmission and receiving coils, varying within the {0; 3R} gap, i.e. {0; 1.5 mm}.

Through a simple quotient of values according to curves 1a and 1b, the curve in FIG. 1c is obtained, thus representing the variations of the $|\delta V_R/V_R|$ ratio when $\Delta_{ER}$ varies within the {0; 1.5 mm} gap. Thus can be read the $|\delta V_R/V_R|_0$ ordinate of the maximum, equal to 0.19 (no dimensions), of which the abscissa corresponding to 0.6 mm is referred to as $\Delta_{ERO}$, such value constituting the optimal operating point of step d. When targeting the sub-optimal operating of step e, the points whose ordinates $|\delta V_R/V_R|$ are equal to 0.63 (the third of the $|\delta V_R/V_R|_0$ maximum) shall be sought after. Then can be read the corresponding abscissa: $\Delta min=0.53$ mm, and $\Delta Max=0.69$ mm, such values being located on either side of $\Delta_{ERO}$.

In practice, optimal operating is chosen, thus leading to fixing $\Delta_{ER}=\Delta_{ERO}=0.6$ mm, in accordance with the embodiment represented in FIGS. 5a and 5b, where the coils in the form of a coil plane, the copper base of which 20 μm wide, have been schematically illustrated by a succession of concentric circles for ease of drawing.

The coils both have a 1 mm external diameter, a 0.5 mm internal diameter and 6 coils; the working frequency is 2 MHz.

The B1 transmitter coil is illustrated at the top and the B2 receiver coil is shown at the bottom, even though the invention would not be altered if they were to be inverted. The isolating base 1 is a soft kapton film 50 μm in thickness. The connections 4 of the coils use metallic holes whenever necessary in order to pass from one side to the other of the dielectric base. Thus all connections are placed on a single face of the printed circuit board.

According to the first preferred variant, the working frequency can be adjusted when the characteristics of the flaws or the type of element to be tested varies. Hence, when the main dimension of the standard flaw to be detected passes from 0.4 mm to 3 mm, the initial frequency of 2 MHz should pass to approximately 2.45 MHz in order to maintain the same $\Delta_{ERO}$ optimal distance.

According to the second preferential variant, the working frequency is fixed, and the optimum $\Delta_{ERO}$ of the $\Delta_{ER}$ distance between the transmitter and receiving coils is determined as explained above in the case of the first variant where the $\Delta_{ER}$ distance between the respective axes $A_1$ and $A_2$ of two coils, respectively $B_1$ transmitter and B2 receiver, varies within a {0; 3R} gap.

In the case of the second variant where such $\Delta_{ER}$ distance varies within a {0; 9R} gap, an analogous method shall be used: the Δmax upper value is simply pushed back from 1.5 mm to 4.5 mm, as shown in FIGS. 2, 3 and 4. The gap chosen during step e, referred to as $\{\Delta min_2; \Delta Max_2\}$, enables to obtain a double $|\delta V_R/V_R|$ value of what it was in the $\{\Delta min; \Delta Max\}$ gap, corresponding to the preceding variant.

At this stage, it is easier to explain about the first preferential embodiment according to which the distance between the respective axes of each transmission/receiving coil combination is fixed and the frequency of the excitation current is adjusted in accordance with the minimal dimension of the average depth of the standard flaws to be detected. If we are to suppose, as before, that the element to be tested has a σ conductivity of 1 MS/m and a thickness of 3 mm, then the coils are air-borne, directly engraved on the two sides of a same supple printed circuit board made in 50 μm-thick kapton. The air-gap e is thus 0.1 mm for the receiving coil with e' equaling 0.15 mm for the transmitter coil. Through modelling are sketched in FIG. 6 the variations of the frequency that the excitation of the inducing coils must have in accordance with the main dimensions of the flaw, when this varies from 0.4 mm (at that time f=2 MHz) to 1 mm, then 2 mm and 3 mm (at that time f=2.45 MHz), in order to maintain an optimum $\Delta_{ERO}$ equaling 0.6 mm on the $\Delta_{ER}$ dimension. When the length of the flaw increases, it is necessary to slightly increase the excitation frequency.

An transmission/receiving coil combination thus defined, significantly improves the detection of type I flaws. It is recalled that the most frequent flaws being generally those extremely elongated according to a main direction, they are filed by type according to the gradient of their largest axis with the plane formed by the A1 and A2 axes of an transmission/receiving coil combination. Thus, they are referred to as type I when their largest axis is found in the plane defined by the A1 and A2 axes, or even parallel and located at a short distance in front of the R radius. They are referred to as type II when their largest axis is found in the orthogonal plane to that defined by the A1 and A2 axes, while being orthogonal to the plane constituted by the surface to be tested.

Preferably, for detecting type I flaws, a receiver coil is placed in a position, such as the electromagnetic field produced by the two transmitter coils being cancelled near to the receiving coil, the distance between the receiving coil and each one of the transmitter coils being comprised around the {Δmin; ΔMax} distance range located around $\Delta_{ERO}$. Nevertheless, such configuration makes detection of the said type-II flaws somewhat difficult.

FIG. 7a illustrates an implementation variant, mainly destined for releasing the edge effects of the elements to be controlled, and possibly for slightly improving the type-II flaws. It comprises a motive constituted of three coils, seemingly a central B1 transmission coil and two B2 and B3 receiving coils, located on either side and distant from the transmission coil by a value comprised within the {Δmin;

ΔMax} range. Nevertheless, performances would not be changed by designating a reception function to the central coil and an transmission function to the two lateral coils. An elementary pattern constituted of three coils, one for reception located in the centre and two for transmission, located on either side and distant from the transmission coil by a value comprised within the {Δmin; ΔMax} range. The coils are all wound in the same direction. In order to make the sketches clearer, the electrical connection have not been illustrated. The method is carried out as mentioned above, and the value found for the distance between the A1 and A2 axes of the B1 transmitter and B2 receiving coils is recorded in an identical manner between the A1 and A3 axes of the B1 transmitter and B3 receiving coils. Advantageously, axes A1, A2 and A3 are all in a same plane.

This pattern, however, only allows the edge effects to be released in the preferred case of the scanning direction, taking place according to a direction that passes through the A2 and A3 axes. Indeed, in such a case, the dissymmetry caused by the element's edge affects the two B2 and B3 receiving coils in the same manner.

Nevertheless, according to another variant, the scanning direction is orthogonal to a direction passing through the A2 and A3 axes, and the mutual dissymmetry caused by the element's edge does not affect the two B2 and B3 receiving coils in the same manner. In such a case, it is important to correct it by introducing, for example at the level of the means for demodulating the signals issued by the B2 and B3 coils, an amplitude and/or phase offset. A symmetry flaw between such coils (systematic error) can also be corrected in this way.

FIG. 7b represents another variant, analogous with that of FIG. 7a, although in this particular case, the coils have an elongated axial section, the widest coil having a large radius $R_M$ and a small radius $R_m$. Within the plane comprising the axis of the coil and the small $R_m$ radius, the application of the invention enables to define a first optimal distance $(\Delta_{ERO})_{min}$ and a range of associated values $\{\Delta min; \Delta Max\}_{min}$. In the case of FIG. 7c, for the plane comprising the axis of the coil and the big $R_M$ radius, the application of the invention enables to define a second optimal distance $(\Delta_{ERO})_{max}$ and a second range of values $\{\Delta min; \Delta Max\}_{max}$.

For the transmission and reception functions able to be inverted, operating is the same when choosing the B1 receiving coil and the two B2 and B3 transmitter coils. In this latter case, the proximity of an element edge inducing a mutual difference between the B1/B2 and B1/B3 coil combinations can be compensated at the level of the means of supply for the B2 and B3 coils via alternating current, generally with amplitude signals and/or varying phases, capable of compensating such dissymmetry. A symmetry flaw between such coils (systematic error) can also be corrected in this way.

Such second embodiment method with a three-coil pattern enables to increase the density of the patterns during scanning according to a direction that is orthogonal to the plane containing the three axes, and thus to improve detection of type-I flaws. On the other hand, it scarcely improves detection of type-II flaws.

In order to control the vicinity of the borders of the elements to be inspected, the plane comprising the three coil axes shall be placed parallel to the edge of the element. It is then possible to wire up the two receiving coils in differential mode, thus enabling to eliminate the interference induced by the nearness of the element's border.

More generally, such a differential configuration minimises the distance variation effects between transmitter and receiving coils, which enables reduced sensitivity to the distance differences during the embodiment of the coils.

Detection of type-II flaws is improved through perfecting the pattern comprising a central B1 coil and the two B2 and B3 transmitter coils on either side. Such perfecting is characterised in that two other receiving coils B4 and B5 are added (FIG. 8a), respectively associated with each transmission coil B2 and B3, at a distance comprised within the {Δmin; ΔMax} distance range, located around $\Delta_{ERO}$ and in a direction more or less perpendicular to the plane passing through the axes of these transmitter coils. These second and third receiving coils enable to detect the elongated flaws according to such perpendicular direction (of type II), the distance between each emitting coil and receiving coil being optimised in order to detect such flaws in this direction. In such a manner, a configuration of five coils is obtained through FIG. 8a, which represents a third embodiment method. Coils B2 (20) and B3 (30) of axes A2 and A3, located on a first face of a printed circuit board, are transmitter coils, receiving electronic excitation means 34 for an alternating current on the chosen excitation frequency. Detection, on the other hand, is ensured by an assembly of three receiving coils B1 (10), B4 (40) and B5 (50) of axes A1, A4 and A5, located on a second face of the printed circuit board and linked to the preamplification and detection means 35. The A2, A3, A1, A4 and A5 axes are parallel to each other. Coil B1 has its A1 axis located preferably in the plane defined by A2 and A3 and necessarily equidistant between these two axes by a distance d contained in the Δd range of distances. The signal emitted is applied at the entry of the first measuring channel.

Coil B4 has its A4 axis located at a distance d, contained in the Δd range of distances, from A2 and defining with A2 a plane that is orthogonal to the plane defined by A2 and A3. Coil B5 has its A5 axis located at a distance d from A3, d contained in the Δd range of distances, and defining with A3 a plane that is orthogonal to the plane defined by A2 and A3. The two B4 and B5 coils are connected in series or facing each other in order to constitute a same signal source, as applied to a second measuring channel of an amplifier 40.

FIG. 8b represents a variant of the coils in FIG. 8a in the particular case where the coils have an elongated axial section, the widest coil having a large radius $R_M$ and a small radius Rm. Within the plane comprising the axis of the coil and the big $R_M$ radius, application of the invention enables to define a first optimal distance $(\Delta_{ERO})_{Max}$ and a range of associated values $\{\Delta min; \Delta Max\}_{Max}$, while within the plane including the coil's axis and the small $R_m$. radius, the invention enables to define a second associated optimal distance $(\Delta_{ERO})_{min}$ and a second range of values $\{\Delta min; \Delta Max\}_{min}$.

More generally, this variant, which can be cumulated with all the aforementioned embodiment methods as well as those hereunder, is characterised in that the transmission and receiving coils have an elongated axial section, the widest coil having on one side a small radius Rm, determining, in accordance with its orientation, a {Δmin; ΔMax} distance range equal to $\{\Delta min; \Delta Max\}_{min}$ in which is chosen the distance between the coils' axes in accordance with such orientation, and on the other side a big radius $R_M$, determining a {Δmin; ΔMax} distance range equal to $\{\Delta min; \Delta Max\}_{Max}$, in which is chosen the distance between the coils' axes in accordance with such orientation.

The preamplification and detection means (35) comprise a first preamplifier receiving signals from the measuring channel emitted by the B1 coil, a first preamplifier receiving signals from the measuring channel emitted by the B4 and B5 coils, and electronic demodulation and processing means. They are designed in such a manner as to determine the difference between the peak values for the existing electromotive forces between the two measuring channels. The forthcoming information possibly improved by its corrections or its filtering, as understood by those skilled in the Art, supplies good detection for all flaws, whatever their orientation. If the test zone is located near to the edge of the element to be tested, the fact of playing on the intensity of currents and their phase enables to eliminate the mutual for each travelling line along the edge of the element.

The fact of planning two B2 and B3 transmitter coils also enables to compensate, by electronic controls, the symmetry flaws between the B2 and B3 coils. To this effect, such compensation is performed by phase and/or amplitude variations.

In these two embodiment methods associated with FIGS. 7 and 8, high dynamics are achieved from the interference signal caused by the flaw; the size of the flaw has further little effect on the optimum spacing between the transmitter coil and the receiver coil. It is to be noted that the optimum operating point of the device can be set by adjusting the supply frequency of the transmitter coil as illustrated in FIG. 6.

In a variant that can be cumulated with all other variants, the lines of the magnetic field can be channeled and the noise signal ratio of the device can be improved by inserting, in the vicinity of the coils and of the side facing the element to be controlled, soft magnetic material (low hysteresis), e.g. ferromagnetic. In this way, the reluctance of the magnetic circuit for each transmission/receiving coil combination shall become significantly reduced. Thus the coupling between the transmitter and the receiver becomes more important and the induced emf becomes greater (not only emf due to the direct coupling the coils, but also the variation of emf due to the flaw). The magnetic material can, for example, be constituted of ferrite sheets. Nevertheless, in the case of a supple insulation base made of kapton, it is preferable to use supple magnetic materials. It may especially use flexible ferrites, ferromagnetic ribbons in permalloy or in nano-crystalline materials (by taking care to electrically insulate such ribbon from the coils of the coils if the ribbon is a conductor). It is also possible to place such soft magnetic material through electrolysis.

FIG. 9 schematically illustrates a variant of the system represented in FIG. 5a comprising the addition of a ferromagnetic ribbon (9) as described above. It channels the magnetic field lines between the transmitter and the receiver. In the event where such ribbon is a conductor, an insulation layer 8 may be inserted in between the ribbon and the printed circuit board engraved on the kapton 1.

FIGS. 10a and 10b schematically illustrate a variant that can be combined with all other variants. The transmitter coils are implanted on a first insulation base 1, the receiving coils (not illustrated) are implanted on a second insulation base 11 in contact with the first, and at least one device enables to modify the $\Delta_{ER}$ distance between the coils of the transmission/reception combination(s).

According to the variant of FIG. 10a, such device is mechanical. The tips of the first insulation base 1 are glued to a tip of base 2 comprising two threaded holes, while the tips of the second insulation base 11 are glued to a tip of base 12 comprising two holes of larger diameter than the threading of base 2. Between the elements 2 and 12 are inserted elastic bands 13 in elastomer, more or less compressed by the screws 14 in order to modify the $A_{ER}$ distance between the axes of each transmission/receiving coil combination.

According to the variant in FIG. 10b, the device enabling to modify the $\Delta_{ER}$ distance between the transmission/receiving coil combinations comprise at least one active mechanical device (a micro-actuator) which enables to modify the $\Delta_{ER}$ distance between the coils and at least one transmission/reception combination. FIG. 10b is thus identical to FIG. 10a, except for the elastic bands 13 which are in this case replaced by piezoelectric micro-actuators 14 supplied by electric conductors 15.

Finally, the invention can be combined with the prior art consisting of associating a plurality of transmission and receiving coils in a single matrix of transducer coils. Each of the previous embodiment methods, or a combination of such methods, can thus be reproduced over and over again in accordance with one or two dimensions, each one representing a measuring step. For such matrix associations, it is especially advantageous to embody the coils by engraving both sides of the printed circuit board. Such embodiments constitute simple transpositions of described examples; it is not necessary to illustrate them in a specific figure.

Advantageously, the two receiving coils assembled to detect the second flaw type, are placed in series or facing one another.

According to a preferred embodiment that can be combined with all the other embodiment methods, except those from FIGS. 5a and 5b, the process according to the invention is implemented using air-borne coils, engraved on a printed supple double-sided circuit board, one of the faces carrying the emitting coils and the other the receiving coils.

Using such a measuring method, a spatial resolution of the flaws is obtained using devices operating under separate functions, such as they exist according to the prior art. Furthermore, the gain is considerable in terms of the $|\delta V_R/V_R|$ parameter, which determines the sensitivity of the method. Finally, there exists a variant enabling to detect the flaws yet more easily, while reducing the lower-size flaws to reach a pre-defined critical size, as well as the artefacts.

We should just like to point out that the choice of a technology for a printed circuit board in order to embody the coils is advantageous for implementing the invention. Such printed circuit board shall be advantageously supple, such as those embodied using kapton, in relation to certain elements to be controlled, taking account of the importance of maintaining a constant very small air-gap.

It is advantageous to use a double-sided printed circuit board, one face carrying the coils destined for transmission, and the other face carrying the coils destined for receiving. If the number of coils of each coil exceeds the space for being engraved on a single face of a circuit board, it is advantageous to use the multi-layer printed circuit boards, some layers carrying coils destined for transmission, and other layers carrying coils destined for receiving.

Finally, this invention can be advantageously combined with a matrix structure for transmission and/or receiving coils. In such a case, the eddy current measuring device comprises a pattern of at least two flat coils B1, B2, according to the invention, such pattern being repeated several times over in such a manner as to constitute a detection matrix, with the associated electronics comprising means for multiplexing the transmitter coils and for demultiplexing the receiving coils. As an example, an embodiment of this type (matrix or bar configuration) is schematically illustrated in FIG. 11. The succession of transmission/receiving coil combinations is organised along two lines, orthogonal in the travelling direction, and shifted laterally by half a step in order to improve the detection probability.

The electronic means of processing the signals emitted from the receiving coils can be constituted by all types of circuit board, thus enabling to measure the emf of a coil in relation to its terminals. Such circuit board possibly comprises one (or several) levels of amplification followed by a level of demodulation destined to remove the excitation frequency of the inducing coil or coils.

If the electronics connected to these coils enable so, the role of the transmission and receiving coils can be inverted for each measure. Such device is especially advantageous in the case of an association of several transmitter/receiving coils in a matrix structure. Inverting the role of the transmission and receiving coils must then be managed by the multiplexing/demultiplexing system.

The invention is compatible with all the existing supply electronics for transmitter coils and for processing signals emitted by the receiving coils. It is simply necessary to check that, when wishing to invert the transmission and reception functions of certain coils, the electronics used accept the coils of a same impedance for these two functions.

The invention claimed is:

1. A method for assembling an assembly of at least one transmission coil and one receiving coil for eddy current testing, the receiving coil receiving, in the absence of a flaw, a complex amplitude signal, $V_R$, subjected to a variation in the presence of a standard flaw to be detected, $\delta V_R$, the method including selecting a distance $\Delta_{ER}$ between respective axes of the transmission and receiving coils that maximizes an absolute value of a ratio of (a) the variation ($\delta V_R$) in the presence of the standard flaw to be detected to (b) the complex amplitude ($V_R$) in the absence of the flaw.

2. A method according to claim 1, in which R is a greatest distance between a baric centre of one of the coils having a dimension larger than the dimension of any other of the coils and a point furthest away from a largest wire winding of the one coil, such method comprising:
a—determining a frequency value of an exitation current running along the transmission coil;
b—determining a further value representing a standard flaw to be detected, characterised by an average size and depth of the standard flaw in relation to a surface to be tested;
c—using the values determined in steps a and b, determining values representing three flaw sizes, either through modelling or by experiment:
i) determining the $V_R$ emf complex induced inside the receiving coil when a distance, $\Delta_{ER}$, between the axes of the transmission and receiving coils varies at least within a {0; 3R} gap,
ii) determining the $\delta V_R$ variation of the $V_R$ emf complex induced inside the receiving coil for the $\Delta_{ER}$ distance variation within the gap of at least {0; 3R},
iii) determining the variation of the ratio $|\delta V_R/V_R|$ for the values obtained in ii) and i), for the $\Delta_{ER}$ distance variation within the gap of at least {0; 3R},
d—determining a course of the $|\delta V_R/V_R|$ ratio curve depending on the $\Delta_{ER}$ distance variation within the gap of at least {0; 3R}, and then determining a maximal $|\delta V_R/V_R|_0$ ordinate and of the $\Delta_{ERO}$ abscissa of this maximum, such value constituting an optimal operating point;
e—as an optimal and sub-optimal solution, determining a range of {Δmin; ΔMax} distances on either side of $\Delta_{ERO}$, for which the $|\delta V_R/V_R|$ ratio corresponds to one third of its maximal value;
f—if the $\Delta_{ER}$ values found during the optimal step d or during the sub-optimal step e are not considered acceptable, then modifying the parameters obtained in steps a and b;
g—adjusting the coils or assembly of the coils, in such a manner that the operating point of each receiving coil corresponds to either the optimal criteria of step d or the sub-optimal criteria of step e.

3. A method according to claim 2, wherein the distance between the respective axes of each transmission/receiving coil combination is fixed and the frequency of the excitation current is adjusted in accordance with a minimal dimension and the average depth of the standard flaws to be detected.

4. A method according to claim 2, wherein the excitation frequency is constant, the method further including the step of determining, according to the minimal dimension and the average depth of the standard flaws to be detected, a value, either optimal (step d) or sub-optimal (step e), of the $\Delta_{ER}$ distance between the respective axes of each transmission/receiving coil combination.

5. A method according to one of the claims 2 to 4, wherein the $\Delta_{ER}$ distance between the respective axes (A1 and A2) of two coils, respectively (B1) transmitter and (B2) receiver, varies within a {0; 3R} gap.

6. A method according to one of the claims 2 to 4, wherein the $\Delta_{ER}$ distance between the respective axes (A1 and A2) of two coils, respectively (B1) transmitter and (B2) receiver, varies within a gap exceeding {0; 3R}, and the method further includes the step of determining for an upper abscissa at 3R a second maximum of the $|\delta V_R/V_R|$ ratio obtained during step d, such second maximum being associated with a second range of values {Δmin; ΔMax}$_2$ on either side of $\Delta_{ERO2}$, obtained during step e, for which the $|\delta V_R/V_R|$ ratio corresponds to one third of its maximal $|\delta V_R/V_R|_2$ value.

7. A method according to claim 2, further including the step of adjusting the $\Delta_{ER}$ distance between the respective axes (A1 and A2) of two coils, respectively (B1) transmitter and (B2) receiver.

8. A method according to claim 7, wherein the step of adjusting the $\Delta_{ER}$ distance includes using mechanical and passive means.

9. A method according to claim 7, wherein the step of adjusting the $\Delta_{ER}$ distance includes using at least one microactuator.

10. A method according to any one of the claims 2 to 4 and 7 to 9, wherein the coils have an elongated axial section, a widest wire winding having a big radius $R_M$ and a small radius $R_m$, and wherein, within the plane including the coil's axis and the big axis $R_M$ define a first optimal distance $(\Delta_{ERO})_{Max}$ and a range of associated values {Δmin; ΔMax}$_{Max}$, while within the plane including the coil's axis and the small axis $R_m$ defines a second associated optimal distance $(\Delta_{ERO})_{min}$ and a second range of values {Δmin; ΔMax}$_{min}$.

11. A method according to any one of the claims to 4 and 7 to 9, wherein the assembly of at least one transmission coil and one receiving coil comprises an elementary pattern constituted of three coils, one transmission coil (B1), located in a central position, and two receiving coils (B2) and (B3), located on either side of the transmission coil and distant from the transmission coil by a value within a range {Δmin; ΔMax}.

12. A method according to any one of the claims to 4 and 7 to 9, wherein the assembly of at least one transmission coil and one receiving coil comprises an elementary pattern constituted of three coils, one receiving central coil (B1) and two transmission coils (B2) and (B3), located on either side and distant from the transmission coil by a value within a range {Δmin; ΔMax}.

13. A method according to any one of the claims 2 to 4 and 7 to 9, wherein the assembly of at least one transmission coil and one receiving coil comprises an elementary pattern constituted of three coils, one receiving central coil (B1) and two transmitter coils (B2) and (B3), located on either side of the receiving coil.

14. A method according to claim 13, wherein the elementary pattern further comprises two other receiving coils (B4 and B5), respectively associated with each transmission coil (B2 and B3), at a distance within the distance range {Δmin; ΔMax} located around $\Delta_{ERO}$ and in a direction approximately perpendicular to a plane passing through the axes of the transmitter coils.

15. A method according to one of the claims 2 to 4 and 7 to 9 and wherein, with reference to step e, the transmission and receiving coils have an elongated axial section, a widest wire winding having, on either side, a small radius Rm, determining, in accordance with its orientation, a {Δmin; ΔMax} distance range equal to {Δmin; ΔMax}$_{min}$ in which is chosen a distance between the wire winding axes in accordance with such orientation, and on the other side a big radius $R_M$, determining a {Δmin; ΔMax} distance range equal to {Δmin; ΔMax}$_{max}$, in which is chosen the distance between the wire winding axes in accordance with such orientation.

16. A method according to one of claims 1 to 4 and 7 to 9, wherein the transmission and the receiving coils constitute a pattern, repeated several times over in such a manner as to create a detection matrix, wherein the assembly is associated with electronic means for excitation and for processing the signals, the excitation and processing comprising multiplexing the signals to the transmitter coils and demultiplexing the signals from the receiving coils.

17. A method according to any one of claims 1 to 4 and 7 to 9, wherein, in the vicinity of the coils and on a side opposite a part to be controlled, exists soft magnetic material serving to reduce the reluctance of the magnetic circuit of each transmission/receiving coil combination.

18. A method according to claim 2, further including the step of, after obtaining a first optimal or sub-optimal value of the $\Delta_{ER}$ distance, readjusting such value according to a plurality of parameter variations by respectively replacing steps c, d and e by the following steps c', d' and e':

c'—using the values obtained during steps a and b, determining, either by modelling or by experiment, the $\delta V_R$ variation of the $V_R$ emf complex induced inside a receiving coil when the $\Delta_{ER}$ distance between the axes of the transmission and receiving coils varies at least within the {0; 3R} gap;

d'—tracing a curve of the $|\delta V_R|$ values according to the $\Delta_{ER}$ distance variation within the gap of at least {0; 3R}, then determining the maximal $|\delta V_R|_0$ ordinate and the $\Delta_{ERO}$ abscissa of this maximum, such value constituting the optimal operating point;

e'—determining a range of {Δmin; ΔMax} distances on either side of $\Delta_{ERO}$, for which the $|\delta V_R|$ ratio corresponds to one third of its maximal value.

* * * * *